(12) United States Patent
Hagerott et al.

(10) Patent No.: US 9,146,248 B2
(45) Date of Patent: Sep. 29, 2015

(54) APPARATUS AND METHODS FOR PURGING FLOW CELLS IN NUCLEIC ACID SEQUENCING INSTRUMENTS

(71) Applicant: INTELLIGENT BIO-SYSTEMS, INC., Waltham, MA (US)

(72) Inventors: Thomas Hagerott, Needham, MA (US); Edmund W. Golaski, Cambridge, MA (US)

(73) Assignee: Intelligent Bio-Systems, Inc., Waltham, MA (US)

( * ) Notice: Subject to any disclaimer, the term of this patent is extended or adjusted under 35 U.S.C. 154(b) by 0 days.

(21) Appl. No.: 13/802,957

(22) Filed: Mar. 14, 2013

(65) Prior Publication Data
US 2014/0259607 A1 Sep. 18, 2014

(51) Int. Cl.
G01N 35/10 (2006.01)
B01L 3/00 (2006.01)

(52) U.S. Cl.
CPC ............ *G01N 35/1004* (2013.01); *G01N 35/10* (2013.01); *B01L 3/502707* (2013.01); *G01N 35/1095* (2013.01); *Y10T 29/49826* (2015.01)

(58) Field of Classification Search
CPC ............................. C12Q 1/6869; G01N 35/02
See application file for complete search history.

(56) References Cited

U.S. PATENT DOCUMENTS

| 5,374,395 | A | 12/1994 | Robinson |
| 5,502,773 | A | 3/1996 | Tibbetts |
| 5,695,934 | A | 12/1997 | Brenner |
| 5,720,923 | A * | 2/1998 | Haff et al. .................... 422/68.1 |
| 5,756,334 | A | 5/1998 | Perler |
| 5,863,722 | A | 1/1999 | Brenner |
| 5,900,481 | A | 5/1999 | Lough |
| 5,981,956 | A | 11/1999 | Stern |
| 6,136,543 | A | 10/2000 | Anazawa |
| 6,207,960 | B1 | 3/2001 | Stern |
| 6,223,128 | B1 | 4/2001 | Allex |
| 6,242,193 | B1 | 6/2001 | Anazawa |
| 6,255,475 | B1 | 7/2001 | Kwiatkowski |
| 6,309,836 | B1 | 10/2001 | Kwiatkowski |
| 6,337,188 | B1 | 1/2002 | Head |
| 6,404,907 | B1 | 6/2002 | Gilchrist |
| 6,448,066 | B1 | 9/2002 | Wheatcroft |
| 6,576,424 | B2 | 6/2003 | Fodor |
| 6,596,483 | B1 | 7/2003 | Choong |
| 6,597,000 | B2 | 7/2003 | Stern |
| 6,611,767 | B1 | 8/2003 | Fiekowsky |
| 6,613,513 | B1 | 9/2003 | Parce et al. |
| 6,639,088 | B2 | 10/2003 | Kwiatkowski |
| 6,646,243 | B2 | 11/2003 | Pirrung |
| 6,664,079 | B2 | 12/2003 | Ju |
| 6,867,851 | B2 | 3/2005 | Blumenfeld |
| 6,890,741 | B2 | 5/2005 | Fan |
| 6,929,944 | B2 | 8/2005 | Matson |
| 7,033,754 | B2 | 4/2006 | Chee |
| 7,037,687 | B2 | 5/2006 | Williams |
| 7,052,847 | B2 | 5/2006 | Korlach |
| 7,057,026 | B2 | 6/2006 | Barnes |
| 7,085,651 | B2 | 8/2006 | Yasuda |
| 7,110,618 | B2 | 9/2006 | Bobrov |
| 7,145,645 | B2 | 12/2006 | Blumenfeld |
| 7,157,228 | B2 | 1/2007 | Hashmi |
| 7,169,560 | B2 | 1/2007 | Lapidus |
| 7,200,254 | B2 | 4/2007 | Kira |
| 7,233,393 | B2 | 6/2007 | Tomaney |
| 7,270,951 | B1 | 9/2007 | Stemple |
| 7,279,563 | B2 | 10/2007 | Kwiatkowski |
| 7,282,337 | B1 | 10/2007 | Harris |
| 7,306,918 | B2 | 12/2007 | Hashmi |
| 7,315,637 | B2 | 1/2008 | Xi |
| 7,329,496 | B2 | 2/2008 | Dower |
| 7,344,865 | B2 | 3/2008 | Parce |
| 7,386,399 | B1 | 6/2008 | Izmailov |
| 7,387,891 | B2 | 6/2008 | Boege |
| 7,405,823 | B2 | 7/2008 | Tomaney |
| 7,414,116 | B2 | 8/2008 | Milton |

(Continued)

FOREIGN PATENT DOCUMENTS

| EP | 1507217 | 2/2005 |
| WO | 0027521 | 5/2000 |

(Continued)

OTHER PUBLICATIONS

International Search Report and Written Opinion for PTC International Application No. PCT/US2014/23474 dated Jul. 14, 2014.

(Continued)

*Primary Examiner* — Gary Benzion
*Assistant Examiner* — David Thomas
(74) *Attorney, Agent, or Firm* — RatnerPrestia

(57) ABSTRACT

A method for operating a nucleic acid sequencing instrument with movable flow cells. The method includes providing a flow cell having a flow path with an inlet port and an outlet port and filling the flow path, from the inlet port to the outlet port, with a first liquid reagent. The method also includes providing a station block having an inlet passage and an outlet passage, mounting the flow cell on the station block with the inlet port in fluid communication with the inlet passage and the outlet port in fluid communication with the outlet passage, introducing a gaseous bubble into the inlet port, conveying a second liquid reagent from the inlet passage into the inlet port to move the gaseous bubble through the flow path and into the outlet passage and fill the flow passage with the second liquid reagent, and removing the flow cell from the station block.

17 Claims, 6 Drawing Sheets

(56) References Cited

U.S. PATENT DOCUMENTS

| | | |
|---|---|---|
| 7,425,416 B2 | 9/2008 | Hashmi |
| 7,427,673 B2 | 9/2008 | Balasubramanian |
| 7,476,504 B2 | 1/2009 | Turner |
| 7,482,120 B2 | 1/2009 | Buzby |
| 7,482,167 B2 | 1/2009 | Sammak |
| 7,491,498 B2 | 2/2009 | Lapidus |
| 7,508,516 B2 | 3/2009 | Sugiyama |
| 7,541,444 B2 | 6/2009 | Milton |
| 7,544,794 B1 | 6/2009 | Benner |
| 7,566,537 B2 | 7/2009 | Balasubramanian |
| 7,566,538 B2 | 7/2009 | Parce |
| 7,567,695 B2 | 7/2009 | Frost |
| 7,592,435 B2 | 9/2009 | Milton |
| 7,635,562 B2 | 12/2009 | Harris |
| 7,635,565 B2 | 12/2009 | Hashmi |
| 7,635,578 B2 | 12/2009 | Ju |
| 7,635,588 B2 | 12/2009 | King |
| 7,666,593 B2 | 2/2010 | Lapidus |
| 7,680,790 B2 | 3/2010 | Indeck |
| 7,687,260 B2 | 3/2010 | Gutekunst |
| 7,713,698 B2 | 5/2010 | Ju |
| 7,714,303 B2 | 5/2010 | Lundquist |
| 7,745,129 B1 | 6/2010 | Schatz |
| 7,771,973 B2 | 8/2010 | Milton |
| 7,785,796 B2 | 8/2010 | Balasubramanian |
| 7,795,424 B2 | 9/2010 | Liu |
| 7,816,503 B2 | 10/2010 | Milton |
| 7,835,871 B2 | 11/2010 | Kain |
| 7,843,567 B2 | 11/2010 | Moon |
| 7,883,869 B2 | 2/2011 | Ju |
| 7,888,073 B2 | 2/2011 | Densham |
| 7,897,345 B2 | 3/2011 | Lapidus |
| 7,993,895 B2 | 8/2011 | Eid |
| 7,994,304 B2 | 8/2011 | Siddiqi |
| 7,998,717 B2 | 8/2011 | Eid |
| 8,012,690 B2 | 9/2011 | Berka |
| 8,018,593 B2 | 9/2011 | Tan |
| 8,022,194 B2 | 9/2011 | Piepenburg |
| 8,030,466 B2 | 10/2011 | Shin |
| 8,031,918 B2 | 10/2011 | Roth |
| 8,032,310 B2 | 10/2011 | Stenger |
| 8,053,192 B2 | 11/2011 | Bignell |
| 8,058,414 B2 | 11/2011 | Menchen |
| 8,071,346 B2 | 12/2011 | Eid |
| 8,071,739 B2 | 12/2011 | Milton |
| 8,084,590 B2 | 12/2011 | Milton |
| 8,088,575 B2 | 1/2012 | Ju |
| 8,094,312 B2 | 1/2012 | Ulmer |
| 8,116,988 B2 | 2/2012 | Glick |
| 8,143,599 B2 | 3/2012 | Feng |
| 8,148,503 B2 | 4/2012 | Litosh |
| 8,158,346 B2 | 4/2012 | Balasubramanian |
| 8,178,360 B2 | 5/2012 | Barnes |
| 8,182,993 B2 | 5/2012 | Tomaney |
| 8,209,130 B1 | 6/2012 | Kennedy |
| 8,212,020 B2 | 7/2012 | Benner |
| 8,236,532 B2 | 8/2012 | Ronaghi |
| 8,241,573 B2 | 8/2012 | Banerjee |
| 8,247,177 B2 | 8/2012 | Smith |
| 8,263,364 B2 | 9/2012 | Williams |
| 8,263,365 B2 | 9/2012 | Williams |
| 8,271,206 B2 | 9/2012 | Liu |
| 8,280,640 B2 | 10/2012 | Levin |
| 8,298,792 B2 | 10/2012 | Ju |
| 8,299,226 B2 | 10/2012 | Piepenburg |
| 8,300,971 B2 | 10/2012 | Osher |
| 8,301,394 B2 | 10/2012 | Chen |
| 8,370,079 B2 | 2/2013 | Sorenson |
| 8,383,039 B2 | 2/2013 | Zhou |
| 8,394,586 B2 | 3/2013 | Balasubramanian |
| 8,399,188 B2 | 3/2013 | Zhao |
| 8,399,196 B2 | 3/2013 | Hoser |
| 8,407,012 B2 | 3/2013 | Erlich |
| 8,407,554 B2 | 3/2013 | Kermani |
| 8,427,637 B2 | 4/2013 | Gao |
| 8,429,108 B2 | 4/2013 | Eusterbrock |
| 8,460,865 B2 | 6/2013 | Chee |
| 8,463,718 B2 | 6/2013 | Ben-Hur |
| 8,481,259 B2 | 7/2013 | Gordon |
| 8,481,903 B2 | 7/2013 | Triener |
| 8,594,951 B2 | 11/2013 | Homer |
| 8,612,161 B2 | 12/2013 | Gordon |
| 8,666,678 B2 | 3/2014 | Davey |
| 8,703,422 B2 | 4/2014 | Tomaney |
| 8,725,425 B2 | 5/2014 | Heiner |
| 8,728,399 B2 | 5/2014 | Jaffe |
| 8,738,300 B2 | 5/2014 | Porreca |
| 8,748,789 B2 | 6/2014 | Triener |
| 8,774,494 B2 | 7/2014 | Staker |
| 8,795,971 B2 | 8/2014 | Kersey |
| 8,812,268 B2 | 8/2014 | Scoullar |
| 8,831,316 B2 | 9/2014 | Tyurina |
| 8,852,910 B2 | 10/2014 | Smith |
| 8,886,535 B2 | 11/2014 | Chong |
| 8,900,810 B2 | 12/2014 | Gordon |
| 8,929,630 B2 | 1/2015 | Fu |
| 8,934,098 B2 | 1/2015 | Cox |
| 8,940,481 B2 | 1/2015 | Gordon |
| 8,965,076 B2 | 2/2015 | Garcia |
| 2001/0030290 A1 | 10/2001 | Stern |
| 2002/0004204 A1 | 1/2002 | OKeefe |
| 2002/0110899 A1 | 8/2002 | Wheatcroft |
| 2003/0087289 A1 | 5/2003 | Zuzan |
| 2003/0215816 A1 | 11/2003 | Sundararajan |
| 2003/0224419 A1 | 12/2003 | Corcoran |
| 2004/0002073 A1 | 1/2004 | Li |
| 2004/0029126 A1 | 2/2004 | Bloecker |
| 2004/0142347 A1 | 7/2004 | Stockwell |
| 2004/0152108 A1 | 8/2004 | Keith |
| 2004/0175718 A1 | 9/2004 | Chee |
| 2004/0185466 A1 | 9/2004 | Ju |
| 2004/0229269 A1 | 11/2004 | Hashmi |
| 2005/0019902 A1* | 1/2005 | Mathies et al. ............ 435/287.2 |
| 2005/0026163 A1 | 2/2005 | Sundararajan |
| 2005/0052509 A1* | 3/2005 | Gilligan et al. ................. 347/85 |
| 2005/0064469 A1 | 3/2005 | Schulz |
| 2005/0170367 A1 | 8/2005 | Quake |
| 2005/0227231 A1 | 10/2005 | Tcherkassov |
| 2005/0239085 A1 | 10/2005 | Buzby |
| 2005/0244827 A1 | 11/2005 | Olsson |
| 2006/0073493 A1 | 4/2006 | Fasulo |
| 2006/0105349 A1 | 5/2006 | Ekenberg |
| 2006/0147935 A1 | 7/2006 | Linnarsson |
| 2006/0166203 A1 | 7/2006 | Tooke |
| 2006/0240439 A1 | 10/2006 | Smith |
| 2006/0275782 A1 | 12/2006 | Gunderson |
| 2006/0281109 A1 | 12/2006 | BarrOst |
| 2007/0048748 A1 | 3/2007 | Williams |
| 2007/0070349 A1 | 3/2007 | Harris |
| 2007/0082358 A1 | 4/2007 | Fuerst |
| 2007/0117103 A1 | 5/2007 | Buzby |
| 2007/0117104 A1 | 5/2007 | Buzby |
| 2007/0177799 A1 | 8/2007 | Tyurina |
| 2007/0196832 A1 | 8/2007 | Efcavitch |
| 2007/0196846 A1 | 8/2007 | Hanzel |
| 2008/0038839 A1* | 2/2008 | Linder et al. ................. 436/501 |
| 2008/0087826 A1 | 4/2008 | Harris |
| 2008/0088823 A1 | 4/2008 | Harris |
| 2008/0103053 A1 | 5/2008 | Siddiqi |
| 2008/0138804 A1 | 6/2008 | Buzby |
| 2008/0161194 A1 | 7/2008 | Turner |
| 2008/0161195 A1 | 7/2008 | Turner |
| 2008/0176241 A1 | 7/2008 | Eid |
| 2008/0182757 A1 | 7/2008 | Heiner |
| 2008/0246949 A1 | 10/2008 | Harris |
| 2008/0280773 A1 | 11/2008 | Fedurco |
| 2008/0293071 A1 | 11/2008 | Gelfand |
| 2009/0056390 A1 | 3/2009 | Falkensson |
| 2009/0099027 A1 | 4/2009 | Greiner |
| 2009/0155793 A1 | 6/2009 | Oliphant |
| 2009/0186771 A1 | 7/2009 | Siddiqi |
| 2009/0263791 A1 | 10/2009 | Ju |
| 2009/0298131 A1 | 12/2009 | Gordon et al. |
| 2009/0325260 A1 | 12/2009 | Otto |

(56) References Cited

U.S. PATENT DOCUMENTS

| | | |
|---|---|---|
| 2010/0009871 A1 | 1/2010 | Reed |
| 2010/0015611 A1 | 1/2010 | Webster |
| 2010/0035253 A1 | 2/2010 | Gordon |
| 2010/0035273 A1 | 2/2010 | Axen |
| 2010/0036110 A1 | 2/2010 | Xie |
| 2010/0041029 A1 | 2/2010 | Ju |
| 2010/0063742 A1 | 3/2010 | Hart |
| 2010/0063743 A1 | 3/2010 | Gordon |
| 2010/0087327 A1 | 4/2010 | Weng |
| 2010/0121582 A1 | 5/2010 | Pan |
| 2010/0143932 A1 | 6/2010 | Lapidus |
| 2010/0152050 A1 | 6/2010 | Gordon et al. |
| 2010/0153420 A1 | 6/2010 | Yang |
| 2010/0159531 A1 | 6/2010 | Gordon |
| 2010/0167413 A1 | 7/2010 | Lundquist |
| 2010/0227327 A1 | 9/2010 | Xie |
| 2010/0235105 A1 | 9/2010 | Volkov |
| 2010/0246977 A1 | 9/2010 | Fu |
| 2010/0311061 A1 | 12/2010 | Korlach |
| 2010/0323350 A1 | 12/2010 | Gordon et al. |
| 2010/0330569 A1 | 12/2010 | Olejnik |
| 2011/0014611 A1 | 1/2011 | Ju |
| 2011/0045489 A1 | 2/2011 | Gardner |
| 2011/0052446 A1 | 3/2011 | Hirano et al. |
| 2011/0081647 A1 | 4/2011 | Siddiqi |
| 2011/0087016 A1 | 4/2011 | Suo |
| 2011/0124054 A1 | 5/2011 | Olejnik |
| 2011/0212437 A1 | 9/2011 | Emig |
| 2011/0220775 A1 | 9/2011 | Triener |
| 2011/0251828 A1 | 10/2011 | Scoullar |
| 2011/0254969 A1 | 10/2011 | Tyurina |
| 2011/0256631 A1 | 10/2011 | Tomaney |
| 2011/0257889 A1 | 10/2011 | Klammer |
| 2011/0268347 A1 | 11/2011 | Staker |
| 2011/0300534 A1 | 12/2011 | Chiou |
| 2012/0020537 A1 | 1/2012 | Garcia |
| 2012/0041727 A1 | 2/2012 | Mishra |
| 2012/0052490 A1 | 3/2012 | Eid |
| 2012/0095201 A1 | 4/2012 | Milton |
| 2012/0109598 A1 | 5/2012 | Davey |
| 2012/0116688 A1 | 5/2012 | Mishra |
| 2012/0156680 A1 | 6/2012 | Ju |
| 2012/0173159 A1 | 7/2012 | Davey |
| 2012/0197623 A1 | 8/2012 | Homer |
| 2012/0252010 A1 | 10/2012 | Balasubramanian |
| 2012/0258869 A1 | 10/2012 | Kersey |
| 2012/0270305 A1 | 10/2012 | Reed |
| 2012/0282708 A1 | 11/2012 | Corbett |
| 2012/0330566 A1 | 12/2012 | Chaisson |
| 2013/0053280 A1 | 2/2013 | Hamasaki |
| 2013/0054171 A1 | 2/2013 | Chen |
| 2013/0060482 A1 | 3/2013 | Sikora |
| 2013/0096015 A1 | 4/2013 | Ju |
| 2013/0116128 A1 | 5/2013 | Shen |
| 2013/0116130 A1 | 5/2013 | Fu |
| 2013/0122485 A1 | 5/2013 | Hong |
| 2013/0137091 A1 | 5/2013 | Gordon |
| 2013/0137110 A1 | 5/2013 | Kraihanzel |
| 2013/0138358 A1 | 5/2013 | Tang |
| 2013/0217006 A1 | 8/2013 | Sorenson |
| 2013/0235388 A1 | 9/2013 | Segale |
| 2013/0260372 A1 | 10/2013 | Buermann |
| 2013/0281321 A1 | 10/2013 | Mann |
| 2013/0289921 A1 | 10/2013 | Gopalan |
| 2013/0301888 A1 | 11/2013 | Gordon |
| 2013/0303384 A1 | 11/2013 | Rearick |
| 2014/0051584 A1 | 2/2014 | Davey |
| 2014/0073514 A1 | 3/2014 | Shen |
| 2014/0073517 A1 | 3/2014 | Zhou |
| 2014/0220558 A1 | 8/2014 | Homer |
| 2014/0222399 A1 | 8/2014 | Davey |
| 2014/0235461 A1 | 8/2014 | Yin |
| 2014/0248618 A1 | 9/2014 | Shaikh |
| 2014/0303016 A1 | 10/2014 | Tomaney |
| 2014/0309143 A1 | 10/2014 | Kersey |
| 2014/0315328 A1 | 10/2014 | Lee |
| 2014/0329694 A1 | 11/2014 | Buermann |
| 2014/0356884 A1 | 12/2014 | Mittal |
| 2015/0038339 A1 | 2/2015 | Gordon |
| 2015/0045234 A1 | 2/2015 | Stone |
| 2015/0080231 A1 | 3/2015 | Staker |
| 2015/0080232 A1 | 3/2015 | Ju |
| 2015/0099642 A1 | 4/2015 | Barany |

FOREIGN PATENT DOCUMENTS

| | | |
|---|---|---|
| WO | 0058507 | 10/2000 |
| WO | 02093144 | 11/2002 |
| WO | 2004018493 | 3/2004 |
| WO | 2004018497 | 3/2004 |
| WO | 2004042403 | 5/2004 |
| WO | 2006074351 | 7/2006 |
| WO | 2008037568 | 4/2008 |
| WO | 2008134867 | 11/2008 |
| WO | 2009085328 | 7/2009 |
| WO | 2011011738 | 1/2011 |
| WO | 2014055963 | 4/2014 |
| WO | 2014165554 | 10/2014 |

OTHER PUBLICATIONS

International Search Report and Written Opinion of PCT International Application No. PCT/US2014/23490 dated Jun. 17, 2014.

Entire patent prosecution history of U.S. Appl. No. 13/832,509, filed, Mar. 15, 2013, entitled, "Flow Cell Alignment Methods and Systems."

* cited by examiner

APPARATUS AND METHODS FOR PURGING
FLOW CELLS IN NUCLEIC ACID
SEQUENCING INSTRUMENTS

BACKGROUND OF THE INVENTION

1. Field of the Invention

The present invention relates to instruments for determining the identity of nucleic acids in nucleotide sequences, and particular examples relate to instruments that use flow cells to conduct sequencing by synthesis or other processes.

2. Description of the Related Art

Over the past 25 years, the amount of DNA sequence information that has been generated and deposited into Genbank has grown exponentially. Many of the next-generation sequencing technologies use a form of sequencing by synthesis (SBS), wherein specially designed nucleotides and DNA polymerases are used to read the sequence of chip-bound, single-stranded DNA templates in a controlled manner. Other next-generation sequencing technologies may use native nucleotides and/or polymerases or labeled oligonucleotides and ligation enzymes to determine nucleic acid sequences. To attain high throughput, many millions of such template spots, each being either single or multiple molecules, are arrayed across a sequencing chip and their sequence is independently read out and recorded. The desire to perform high throughput sequencing stems from the need for faster processing and reduced costs. However, commercial high throughput systems, while reducing the cost of large scale sequencing (e.g. 10-100 gigabases), make smaller scale sequencing (e.g. 100 megabases to 1 gigabase) costly and inconvenient.

Recently, instruments have been developed to perform sequencing on a much smaller scale than conventional devices. Exemplary apparatus and methods that may be used for performing smaller scale sequencing operations are described in U.S. Patent Publication Nos. 2010/0323350 (application Ser. No. 12/719,469, filed Mar. 8, 2010), 2010/0152050 (application Ser. No. 12/704,842, filed Feb. 12, 2010), and 2009/0298131 (application Ser. No. 12/370,125, filed Feb. 12, 2009). The foregoing are incorporated herein by reference. Such instruments use an "assembly line" type system, which may be arranged in the form of a carousel, to simultaneously process a number of relatively small flow cells. During operation, each flow cell is physically moved through a series of processing stations. Some of these processing stations purge the flow cell and fill it with a new reagent, while others are used for imaging the flow cell, or as idle stations where the flow cell is held without substantive processing. Other processing stations may also be provided. These instruments provide high throughput SBS operations, while offering significant savings in reagents and other processing costs. This new generation of instruments is expected to expand the public's access to SBS operations to use for various purposes, at a reduced cost, and with more rapid turnaround than earlier devices could offer.

There continues to be a need to advance the state of the art of sequencing instruments, and particularly those that use movable flow cells for small-scale sequencing operations.

SUMMARY

In one exemplary embodiment, there is provided a method for operating a nucleic acid sequencing instrument having one or more movable flow cells. The method includes providing a flow cell having a flow path with an inlet port and an outlet port, and filling the flow path, from the inlet port to the outlet port, with a first liquid reagent. The method also includes providing a station block having an inlet passage and an outlet passage, and mounting the flow cell on the station block to place the inlet port in fluid communication with the inlet passage and the outlet port in fluid communication with the outlet passage. The method also includes introducing a gaseous bubble into the inlet port, conveying a second liquid reagent from the inlet passage into the inlet port to move the gaseous bubble through the flow path and into the outlet passage and fill the flow passage with the second liquid reagent, and removing the flow cell from the station block.

In another exemplary embodiment, there is provided another method for operating a nucleic acid sequencing instrument having one or more movable flow cells. This embodiment comprising providing a flow cell having a flow path with an inlet port and an outlet port, providing a first station block having a first inlet passage and a first outlet passage, and providing a second station block having a second inlet passage and a second outlet passage. The process includes mounting the flow cell on the first station block to place the inlet port in fluid communication with the first inlet passage and the outlet port in fluid communication with the first outlet passage, pumping a first liquid reagent from the first inlet passage into the inlet port to fill the flow path with the first liquid reagent, and removing the flow cell from the first station block. The method further includes mounting the flow cell on the second station block to place the inlet port in fluid communication with the second inlet passage and the outlet port in fluid communication with the second outlet passage, introducing a gaseous bubble into the inlet port, pumping a second liquid reagent from the second inlet passage into the inlet port to move the gaseous bubble from the inlet port to the second outlet passage and to fill the flow path with the second liquid reagent, and removing the flow cell from the first station block.

The recitation of this summary of the invention is not intended to limit the claims of this or any related or unrelated application. Other aspects, embodiments, modifications to and features of the claimed invention will be apparent to persons of ordinary skill in view of the disclosures herein.

BRIEF DESCRIPTION OF THE DRAWINGS

A better understanding of the exemplary embodiments may be understood by reference to the attached drawings, in which like reference numbers designate like parts. The drawings are exemplary and not intended to limit the claims in any way.

DETAILED DESCRIPTION

The exemplary embodiments described herein relate to apparatus and methods for purging reagents from flow cells used in small-scale sequencing by syntheses (SBS) instruments. While embodiments describe herein are believed to have particular utility in the foregoing application, other uses for the apparatus and methods will be apparent to persons of ordinary skill in the art in view of the present disclosure and upon practice of the invention. For example, embodiments may find utility in other kinds of instruments that periodically disengage a flow cell from a processing station block were fluids are introduced to the flow cell. Thus, the following examples are not intended to be limiting examples of the scope of the invention.

Figure 1:
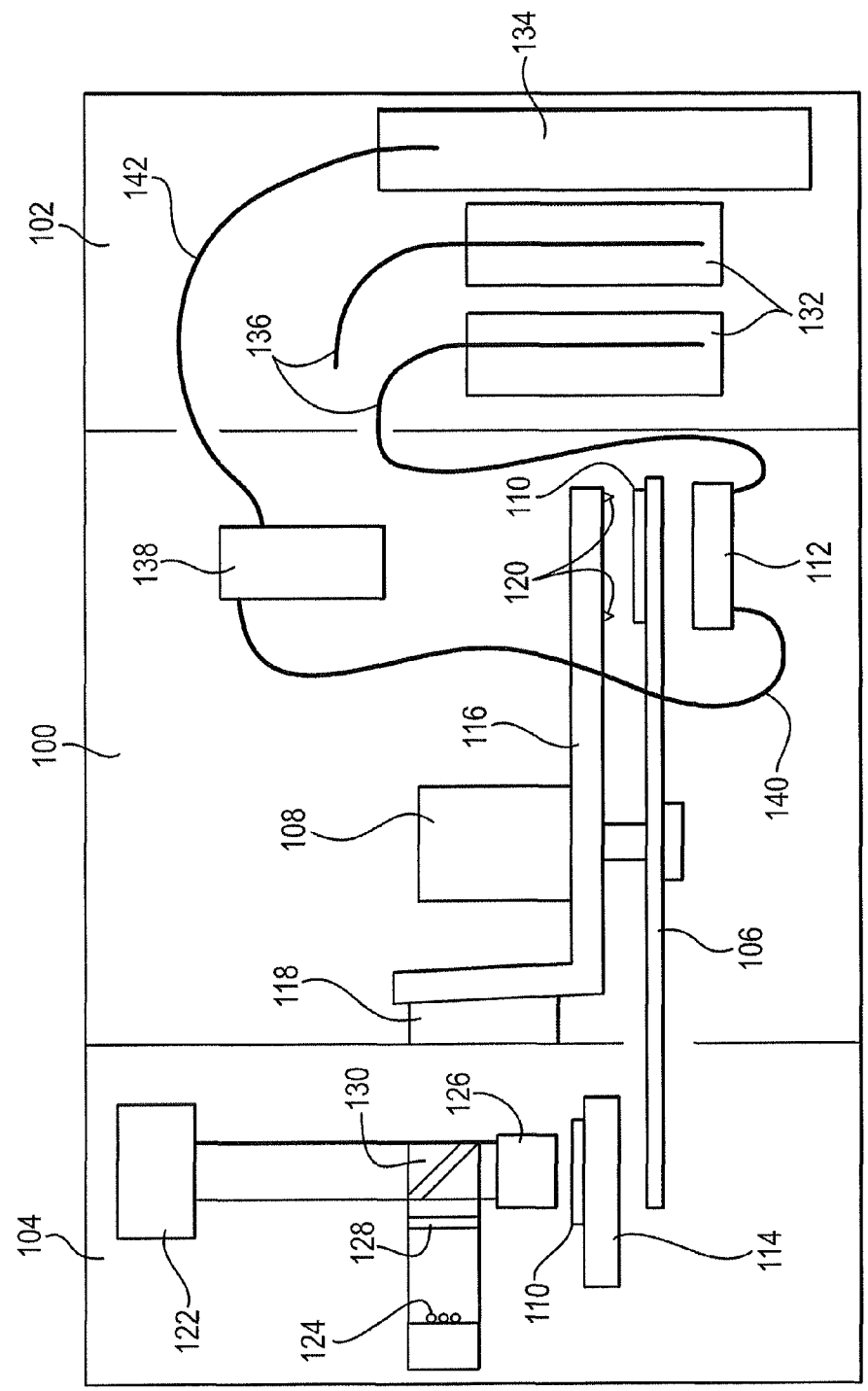
FIG. 1 is a schematic front view of a sequencing instrument

FIG. 1 is a front schematic view of an instrument configured for performing small-scale SBS processing simultaneously on multiple flow cells. The instrument includes a main processing chamber 100, a reagent chamber 102, and an imaging chamber 104. The chambers may be covered by exterior housings to prevent intrusion during automated operation, as known in the art. It will be appreciated that the use of separated chambers and the particular layout shown in FIG. 1 are not required in all embodiments.

The main processing chamber 100 includes a carousel 106 that is rotated by a carousel motor 108. The carousel 106 is configured to transport flow cells 110 around a circular path to various processing stations, such as one or more station blocks 112 and an imaging station 114. The carousel 106 and carousel motor 108 may be mounted on an elevator platform 116 that is driven in the vertical direction by an actuator 118. When the carousel 106 is properly oriented with the flow cell 110 over a station block 112, the actuator 118 moves the carousel 106 down to deposit the flow cell 110 on the station block 112. The elevator platform 116 may include one or more clamps 120, such as spring-loaded plungers, to hold the flow cell 110 in place on the station block 112.

The imaging station 114 may comprise a separate movable platform that holds and manipulates the flow cell 110 for imaging by a camera 122. Various optical devices may be used in conjunction with the imaging station 114, such as lenses 124, a light source 126 (e.g., banks of LEDs, lasers, or the like), a light source filter 128, and a dichroic mirror 130 to filter out light of certain wavelengths.

Each station block 112 may be configured to perform one or more operations, such as heating, cooling, introducing liquid reagents, idling, and so on. One or more of the station blocks 112 are configured to pass liquid reagents through the flow cell 110. To this end, the reagent chamber 102 holds one or more reagent containers 132, and one or more waste containers 134. Each reagent container 132 is connected to one or more station blocks 112 by a system of supply hoses 136. One or more pumps 138 (e.g., syringe pumps, peristaltic pumps, or the like) are used to convey the reagents to the station blocks 112. In this case, a single pump 138 is connected to the station blocks 112 by a system of suction hoses 140. The pump 138 conveys the used reagents to the waste container 134 by a waste hose 142.

Figure 2:
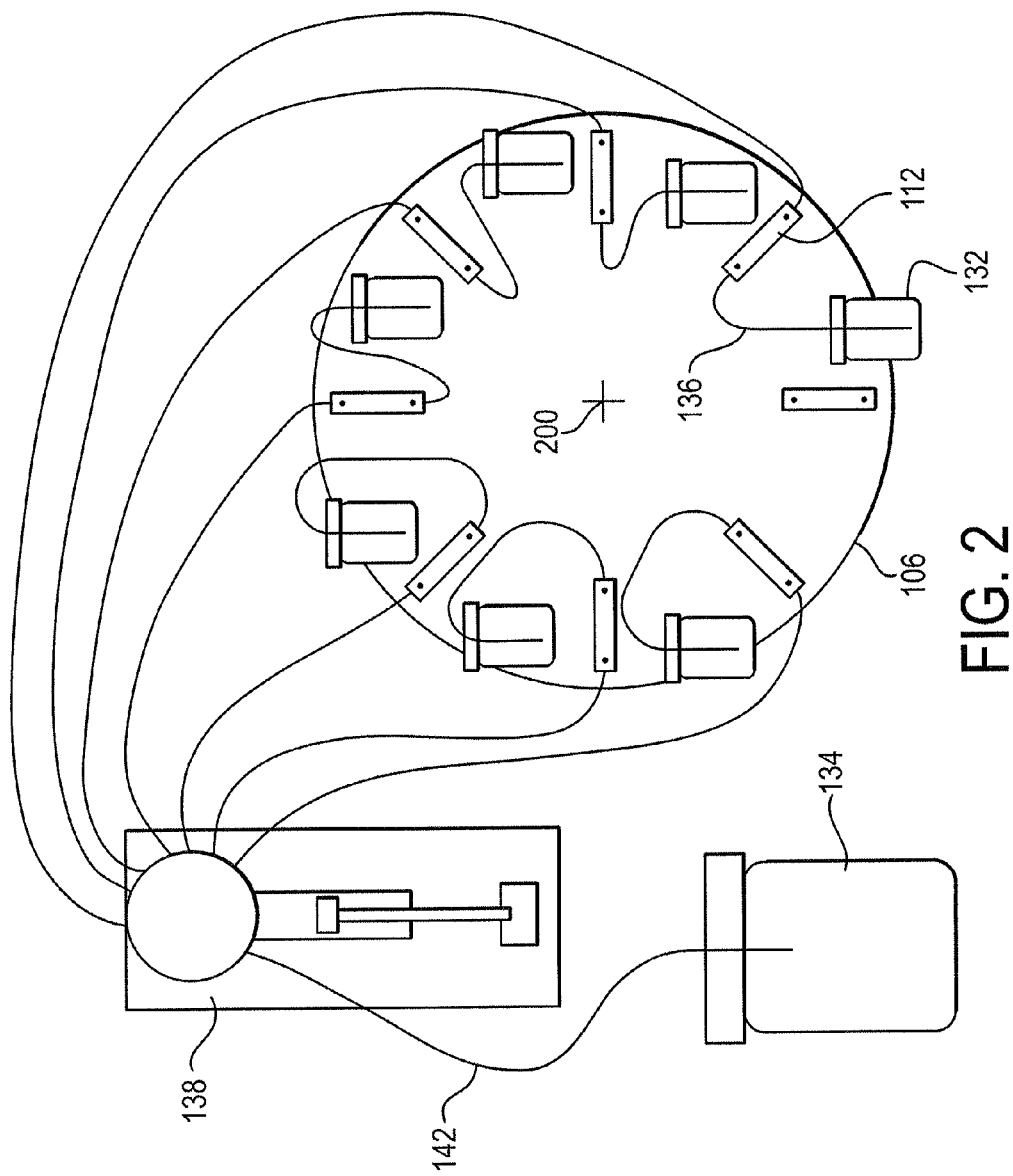
FIG. 2 is another schematic view of the sequencing instrument of FIG. 1.

FIG. 2 illustrates how the carousel 106 overlies a plurality of station blocks 112. The station blocks 112 are arranged in a radial pattern around the carousel's rotation center 200, so that the carousel 106 can move the flow cells progressively along the station blocks 112 without adjusting the flow cells' angular or radial position on the carousel 106. FIG. 2 illustrates each station block 112 having its own reagent container 132, and a single pump 138 conveying all of the used reagents to a single waster container 134. Other embodiments may use different numbers of reagent containers 132, waste containers 134 and pumps 138. It is also envisioned that embodiments may use non-circular conveyor systems, such as linear actuators to move the flow cells 110 along a straight line of station blocks 112, and so on.

Details on operating an instrument such as the one described above, as well as many possible variations on the instrument's construction, are described in copending U.S. application Ser. No. 12/719,469 (hereinafter "Gordon et al."), filed Mar. 8, 2010 (Publication No. US 2010/0323350), which is incorporated herein by reference. Examples of variations include using a positive pressure in the reagent containers 132 to move the reagent through the flow cells, recycling reagents after they leave the flow cells 110, and so on. Other variations and modifications will be apparent to persons of ordinary skill in the art in view of the present disclosure.

The reagents used in the instrument may vary depending on the particular application. Examples of reagents include those described in Gordon et al. and others. For example, the reagents may include: nucleic acid sequencing reagents, nucleotide "cocktails" and polymerase mixtures, de-blocking (cleaving) reagents (enzymes or compounds capable of removing protective groups in order to permit nucleic acid extension by a polymerase), label removing (cleaving) agents (enzymes or compounds capable of removing fluorescent labels), wash reagents, wash buffers, blocking buffers, cleaving agent scavengers, oxygen scavengers, purified water, and so on. Other versions of the instrument may use other reagents, and other embodiments are not intended to be limited to the foregoing list or other reagents specifically identified herein except as where stated to the contrary.

Figure 3:
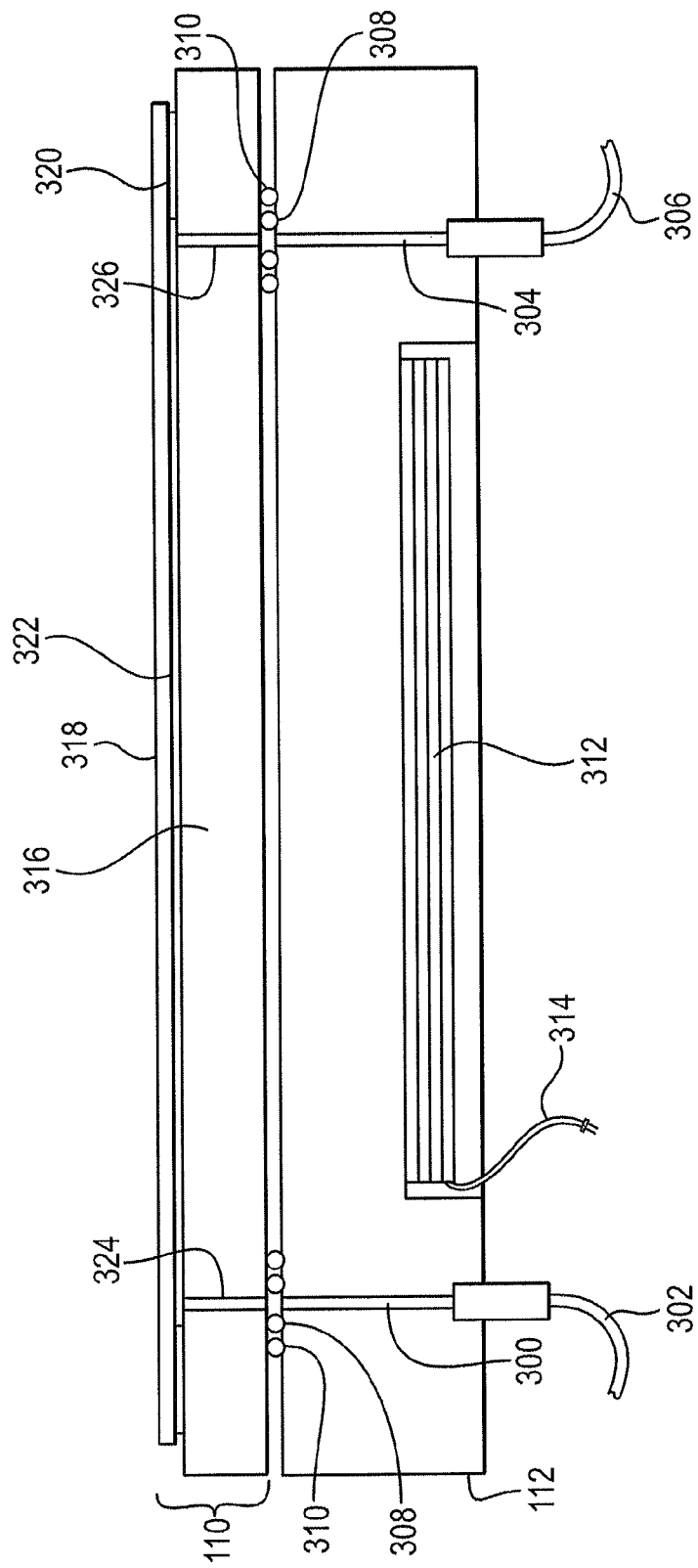
FIG. 3 is a cross-section side view of an exemplary station block mounting an exemplary flow cell.

FIG. 3 illustrates a station block 112 for transiently mounting a removable flow cell 110. The station block 112 includes an inlet passage 300 that receives reagent from an inlet hose 302, and an outlet passage 304 that directs used reagent to an outlet hose 306. The upper face of the station block 112 is configured to receive the flow cell 110, and preferably is machined flat. If desired, the station block 112 and flow cell 110 may include corresponding structures (e.g., pins and holes) to help position the flow cell 110 at a desired location on the station block 112. The upper face of the station block 112 may include one or more seals, such as radially-spaced inner and outer O-rings 308, 310, surrounding the inlet passage 300 and the outlet passage 304, as described in Gordon et al. The station block 112 also may include resistive heating or thermoelectric heating/cooling temperature control elements 312 that are in communication with a power source via wires 314 or the like, to maintain the station block 112 at a desired temperature. A thermocouple (not shown) may be integrated into or associated with the station block 112 or the temperature control element 312 to provide feedback control of the station block's temperature.

The exemplary flow cell 110 comprises a base plate 316 and a top cover 318. The top cover 318 is joined to the base plate 316 by a spacer film 320 that provides a flow path 322 between the top cover 318 and the base plate 316. The spacer film 320 may also form a fluid seal around the perimeter of the flow path 322. The base plate 316 includes an inlet port 324 and an outlet port 326. The inlet port 324 and outlet port 326 are positioned to be in fluid communication with the inlet passage 300 and outlet passage 304, respectively, when the flow cell 110 is mounted on the station block 112, and may be located in direct registration, such as shown. The top cover 318 preferably is transparent to radiation used to detect nucleotide sequencing dyes or the like. For example, the top cover 318 may comprise a transparent glass plate. Variations on this construction may be used in other embodiments. For example, the spacer film 320 may be replaced by a layer of adhesive or a ridge on the upper face of the base plate 316, or the flow path 322 may be machined, etched or otherwise formed as a groove in the base plate 316 and/or top cover 318. Other variations and modifications are described in Gordon et al., and still other variations and modifications will be apparent to persons of ordinary skill in the art in view of the present disclosure.

As described in Gordon et al., the flow cells 110 are processed by successively engaging the flow cell 110 with a series of station blocks 112. At some or all of the station blocks 112, reagent may be pumped into the flow cell to conduct the particular operation desired at that station block 112. After the operation is complete, the flow cell 110 is removed from the station block 112 and moved to the next. The reagent from each station block 112 remains in the flow path 322 of the flow cell 110 until it is flushed out by the reagent pumped in at the next station block 112. For example, a nucleic acid sequencing reagent pumped into the flow path 322 at one station block 112 may remain in place until a wash buffer is introduced at the next station block 112 to flush it out. Gordon et al. explains that the flow cell 110 may be constructed with valves, a horizontal passage, or small dimensions to prevent fluid from draining out of the flow cell 110 between station blocks 112. Gordon et al. also describes a preference for preventing reagent from flowing back to the reagent containers 132 whenever a flow cell 110 is removed from a station block 112, such as by using check valves of the like to prevent such flow. In use of a device similar to that shown in Gordon et al., it has been found that the small dimensions of the inlet port 324 and outlet port 326 are sufficient to prevent reagent from leaving the flow cell 110 as it travels between successive station blocks 112.

The foregoing operation—i.e., maintaining the fluid level in the station blocks 112 and preventing reagent from escaping from the flow cells 110 during transport—prevents air from being introduced into the flow cells 110 during the series of processing steps. In practice, this result was considered desirable to prevent any of the millions of nucleic acids in the flow cell 110 from being dislodged or flushed out by turbulence that could potentially be created by a bubble of air passing through the flow path 322. Such disturbances would decrease the accuracy and usefulness of the data collected by the instrument, because the instrument relies on precisely mapping the locations of each nucleic acid sequence fixed to the flow cell 110. Furthermore, it is well-known that exposing the nucleic acids to air can dry them out and "kill" them by preventing further useful chemical reactions.

In contrast to prior conceptions, it is believed that deliberately introducing a gaseous bubble into the flow cell 110 between one or more reagent flows can have a particularly beneficial effect that overcomes any risk that a population of nucleic acids under investigation will be "killed," displaced, or removed by the bubble. It is also believed that the size of this population may be minimal or even virtually undetectable.

Figure 4:
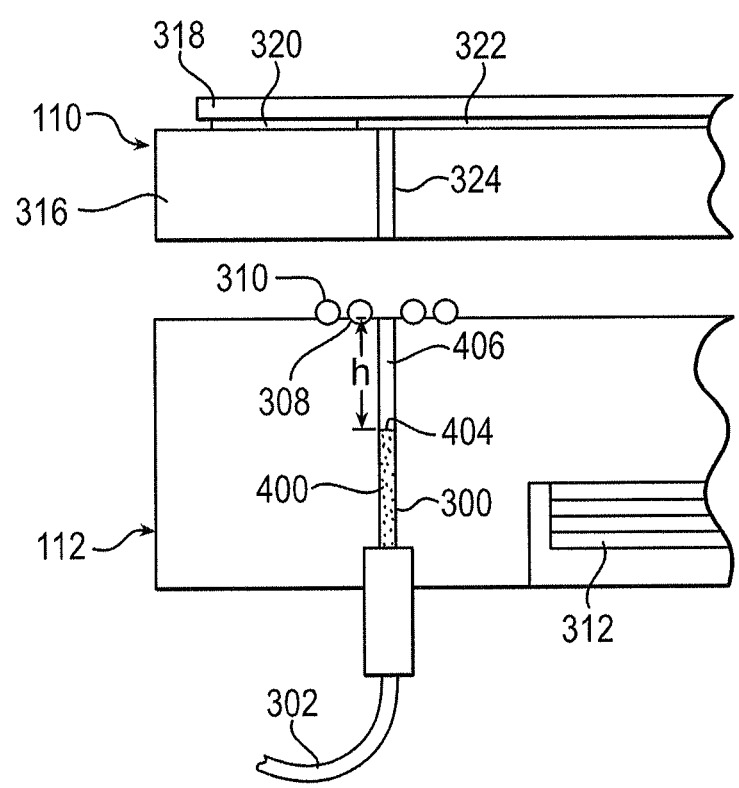
FIG. 4 is a detailed view of an inlet side of an exemplary station block and flow cell.

A process for introducing an gaseous bubble into the flow cell 110 is now described with reference to FIG. 4, which is a detailed view of an inlet side of an exemplary station block 112 and flow cell 110. In this process, liquid reagent 400 is provided in the station block's inlet passage 300. In a conventional operation, the liquid reagent 400 fills the inlet passage 300 to be as close as possible to the upper face 402 of the station block 112, and may overfill the inlet passage 300 to reside in the area bounded by the O-rings 308, 310. In the process of FIG. 4, however, the liquid reagent 400 is lowered such that the upper extent 404 (e.g., meniscus or layer of bubbles) of the liquid reagent 400 is spaced from the upper surface by a distance h, leaving a gas space 406 in the inlet passage 300 above the liquid reagent 400 that is filled by a gas. The gas in the gas space 406 may comprise ambient air, gasses emitted from the liquid reagent 400, or other gaseous phase substances (e.g., purified oxygen).

Figure 5:
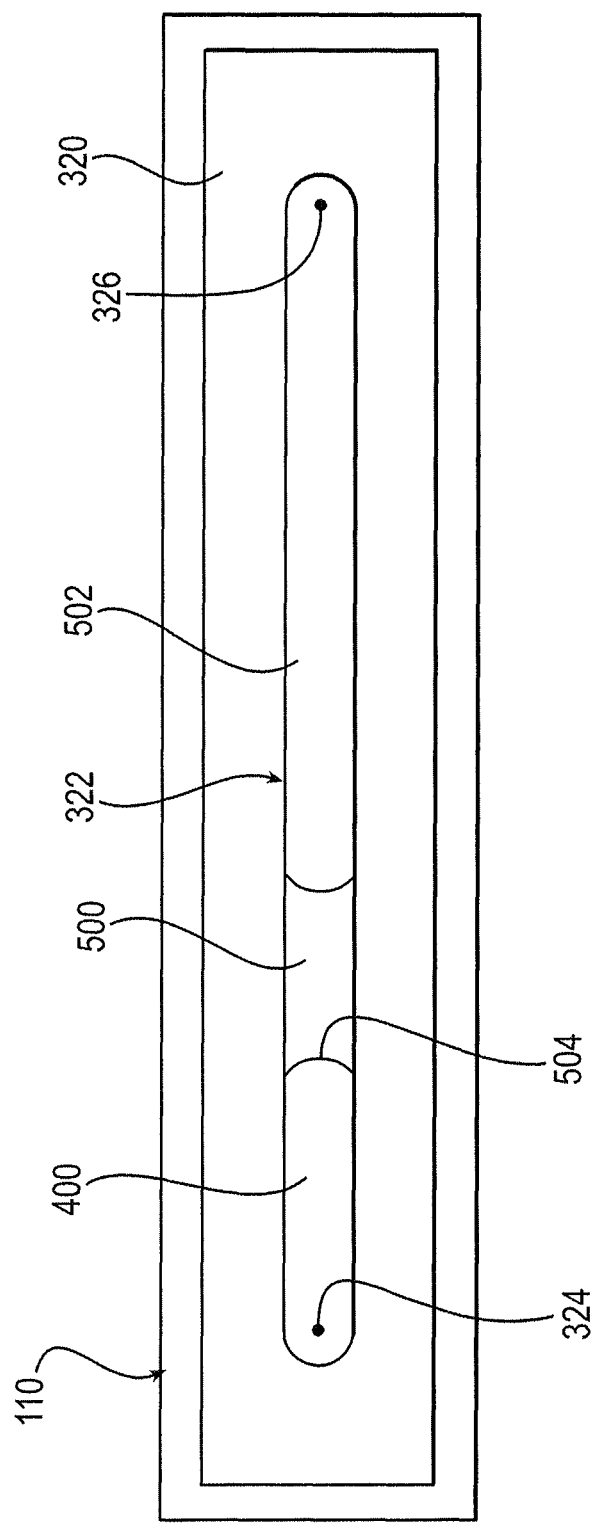
FIG. 5 is a top view of the flow cell of FIG. 4.

Once the gas space 406 is formed in the inlet passage 300, the pump 138 or other means (e.g., gravitational flow, positive pressure gas in the reagent container 132, etc.) moves the liquid reagent 400 into the flow cell 110 through the inlet port 324. The O-rings 308, 310 or other seal prevents the gas from escaping. Thus, as shown in FIG. 5, the incoming liquid reagent 400 conveys the gas as a bubble 500 into the flow path 322 ahead of the liquid reagent 400.

Passing the gas bubble 500 through the flow path 322 is expected to provide several benefits. First, the bubble 500 is expected to act as a physical barrier between the incoming liquid reagent 400 and the outgoing used liquid reagent 502. This minimizes direct contact between and mixing of the two reagents, thereby inhibiting back-flow and dispersion of the used reagent 502 into the new reagent 400. In addition, it is believed that the meniscus 504 of the incoming liquid reagent 400 may act as a wiper to sweep away particles, molecules and droplets that remain from the outgoing liquid reagent 502. This phenomenon may be caused if the surface tension of the molecules in the incoming liquid reagent 400 is sufficient to drive the leftover reagent particles and droplets ahead of the meniscus 504. FIG. 5 illustrates the incoming liquid reagent 400 with a convex meniscus 504, but the same phenomenon may occur if the meniscus 504 is convex. It will be appreciated that the foregoing explanation is one effort to explain the expected operational phenomena, but the invention is not intended to be limited to any particular theory of operation.

The reduction in mixing and backflow, and the possible sweeping effect of the incoming meniscus, is expected to further reduce reagent waste by more efficiently purging the used reagent from the flow path 322. In prior methods, the purging process would account for mixing during the purging process, so incoming reagent continued to flow long enough to make sure the flow path 322 did not include a mixture of new and old reagents. By using a gas bubble 500 to separate the reagents 400, 502, it may not be necessary to continue the reagent flow as long as it ordinarily would to fully purge the old reagent from the flow path 322. To strive towards this goal, one embodiment may introduce a gaseous bubble 500 having a volume of at least about 2 microliters, which is expected to fully prevent contact between the incoming liquid reagent 400, and the main mass (i.e., all but any leftover particles, drops or the like) of the outgoing reagent 502. Other embodiments may use gaseous bubbles 500 having a different size, depending on the size of the flow path 322 and other dimensions. It is expected that the best results will be obtained when the diameter of the air bubble (a measured in the width direction in the flow path 322) is equal to or greater than the width of the flow path 322 at its widest point, as this should provide full separation between the two liquids. However, other sizes may be used, and it is contemplated that a single gaseous bubble 500 may be replaced by multiple smaller bubbles, or a series of larger bubbles.

It is contemplated that the gaseous bubble 500 may be formed using any suitable method. Non-limiting examples are described below.

In the embodiment of FIG. 4, a gas space 406 may be formed using a conventional station block 112 by evaporating a portion of the liquid reagent 400 before the flow cell 110 is mounted in the station block 112. In normal use, one or more of the station blocks 112 may be heated, typically to temperatures between 37°-70° Celsius (98°-158° Fahrenheit). In such cases, however, the heated station blocks 112 typically are in constant use, and only unoccupied for as much time as it takes to remove one flow cell 110 and replace it with another. Thus, in normal use, there is insufficient time to evaporate any appreciable amount of liquid reagent 400 before a new flow cell 110 is mounted on the station block 112 (and if there was time for evaporation, it would have been considered a problem requiring refilling to prevent the creation of a bubble).

To deliberately form a gas space 406, the station block 112 may be heated, in the absence of a flow cell 110, for sufficient time to induce evaporation to form the desired volume of gas space 406. This process may also help degas the liquid reagent 400, which may be helpful to prevent the later formation of gas bubbles in the flow path 322 during imaging or chemical reactions. Where degassing occurs, it may result in a layer of fine bubbles at the upper extent 404 of the liquid reagent 400, and these may assist with the sweeping function described above. It may be possible to induce the desired evaporation without any heating (i.e., at ambient temperature), but it is more preferable and may be necessary in practice to induce heating using a pre-existing temperature control element 312, or a dedicated heating element that focuses heat directly on the liquid reagent 400 (e.g., a separate heater surrounding the inlet passage 300). For example, it is believed that a pre-existing temperature control element 312 such as shown in FIG. 3 may be used to induce sufficient evaporation to obtain a gas space 406 by operating it at a temperature of about 65° Celsius (about 150° Fahrenheit) for about 15 seconds before placing a flow cell 110 on the station block 112. Other embodiments may deviate from this example. For example another embodiment may operate at a temperature of about 140° to about 150° degrees Fahrenheit for a period of about 7.5 to about 15 seconds.

Figure 6:
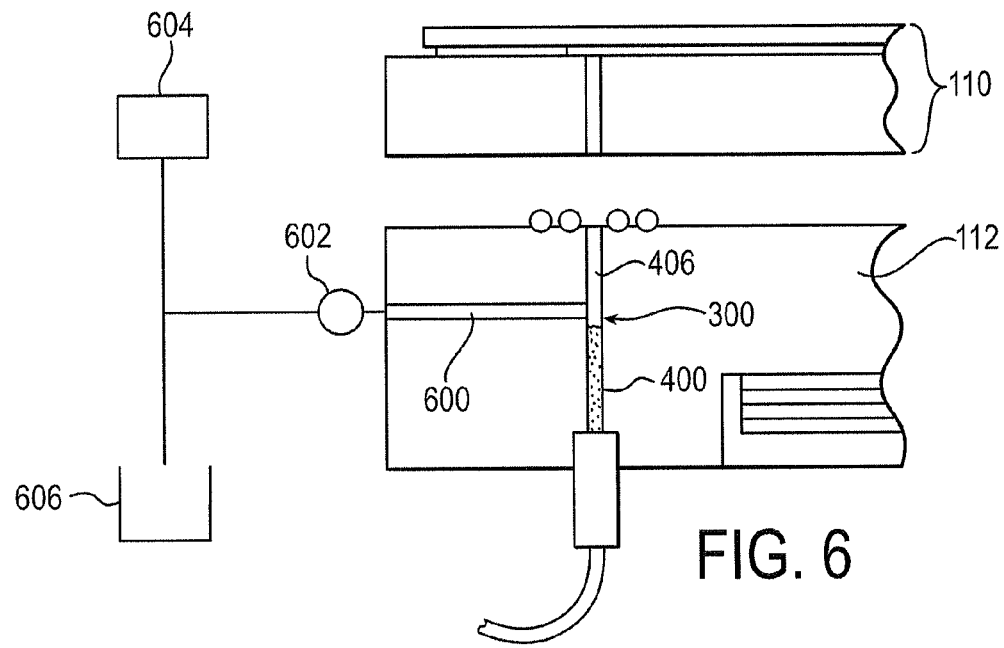
FIG. 6 is a detailed view of the inlet side of another exemplary station block.

FIG. 6 illustrates another embodiment for creating a gas space 406 above the liquid reagent 400. In FIG. 6, the station block 112 includes an auxiliary passage 600 in fluid communication with the inlet passage 300. The auxiliary passage 600 is connected to a valve 602 and a source of pressurized gas, such as an air pump 604 or nitrogen cylinder. When the flow cell 110 is connected to the station block 112, the valve 602 is opened to admit enough air (or other gas) to create a gas bubble of the desired size. An alternative embodiment of FIG. 6 may instead use the auxiliary passage 600 as a vent to drain a quantity of liquid reagent 400 from the inlet passage 300 before each flow cell 110 is placed on the station block 112. In this embodiment, the valve 602 may be opened to drain the liquid reagent 400 into a reservoir 606 or back into the original reagent container 132.

Figure 7:
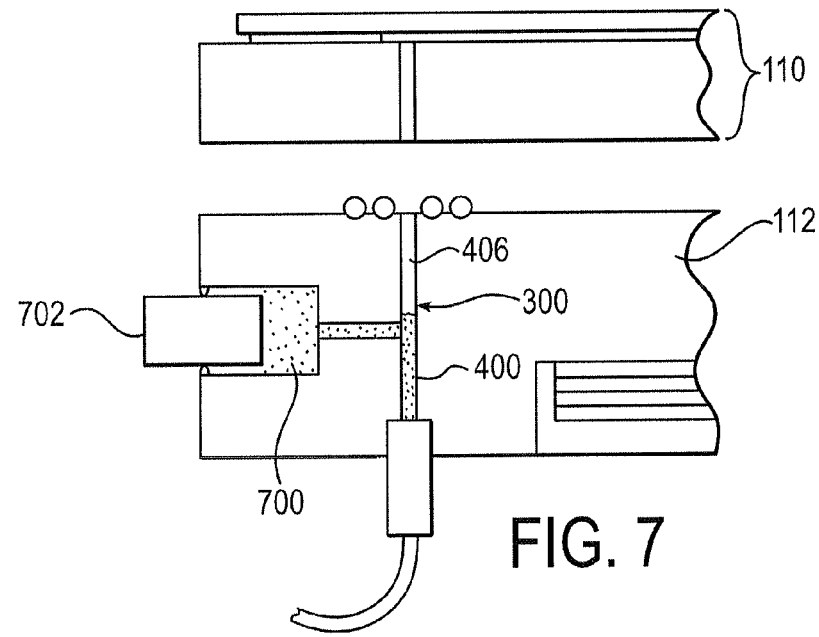
FIG. 7 is a detailed view of the inlet side of still another exemplary station block.

Another exemplary embodiment for creating a gas space 406 is shown in FIG. 7. Here, the station block 112 includes a variable-displacement chamber 700 located in fluid communication with the inlet passage 300. The volume of the variable-displacement chamber 700 is regulated by a piston 702. The piston 702 may be operated by a dedicated drive, such as a solenoid or drive motor, or by other means. In use, each time a flow cell 110 is removed from the station block 112, the piston 702 is moved to expand the volume of the variable-displacement chamber 700, thereby pumping a portion of the liquid reagent 400 in the inlet passage 300 back into the variable-displacement chamber 700 and leaving a gas space 406 in the inlet passage 300. After the next flow cell 110 is installed on the station block 112, the piston 702 is moved to contract the variable-displacement chamber 700. This may be done before, during or after the pump 138 operates to begin the flow of the liquid reagent 400 into the flow cell 110. The piston 702 keeps the variable-displacement chamber 700 in the contracted state until the flow cell 110 is removed, and then the cycle begins again. It will be appreciated that the variable-displacement chamber 700 may comprise a syringe-like arrangement, a flexible bladder that is compressed by a piston or clamp, and so on.

Other embodiments may use other methods and mechanisms to create a gas space 406. For example, a pump located upstream of the inlet passage 300 may be pumped in reverse to draw the liquid reagent 400 backwards to create the gas space 406. Or, the liquid reagent 400 may be flowed backwards by gravity, if the reagent container 132 is located below the inlet passage 300, under the control of a valve.

In other embodiments, a gas bubble 500 may be introduced directly in the flow cell 110. For example, gas could be injected directly into the inlet port 324 at a separate station block 112 dedicated to introducing gas into the flow cells 110. As another example, the flow cells 110 may include a dedicated port, separate from the inlet port 324, for injecting gas into the flow path 322. As yet another example, the flow cell 110 may be designed to drip reagent out into a waste tray or reservoir as it is moved from station block to station block, or it may be tilted at predetermined locations to use gravity to draw out some or all of the used reagent 502. In still another example, air may be introduced by momentarily breaking the seal at the flow cell inlet port 324 just as the pump begins drawing the new reagent 400 into the flow path 322.

Other variations and modifications for providing a gaseous bubble 500 into the flow path 322 will be apparent to persons of ordinary skill in the art in view of the present disclosure. It will also be appreciated that embodiments of methods and apparatus may be adapted for use in sequencing instruments that have fixed flow cells, rather than movable flow cells as described in Gordon et al.

The present disclosure describes a number of new, useful and nonobvious features and/or combinations of features that may be used alone or together. The embodiments described herein are all exemplary, and are not intended to limit the scope of the inventions. It will be appreciated that the inventions described herein can be modified and adapted in various and equivalent ways, and all such modifications and adaptations are intended to be included in the scope of this disclosure and the appended claims.

What is claimed is:

1. A method for operating a nucleic acid sequencing instrument having one or more movable flow cells, the method comprising:
   providing a flow cell comprising a flow path having an inlet port and an outlet port;
   filling the flow path, from the inlet port to the outlet port, with a first liquid reagent;
   providing a station block having an inlet passage and an outlet passage;
   mounting the flow cell on the station block to place the inlet port in fluid communication with the inlet passage and the outlet port in fluid communication with the outlet passage;
   introducing a gaseous bubble into the inlet port by:
      evaporating a portion of a second liquid reagent located in the inlet passage to create a gas space at a top end of the inlet passage prior to mounting the flow cell on the station block, and
      capturing gas in the gas space upon mounting the flow cell to the station block to thereby form the gaseous bubble;
   conveying a second liquid reagent from the inlet passage into the inlet port to move the gaseous bubble through the flow path and into the outlet passage and fill the flow passage with the second liquid reagent; and
   removing the flow cell from the station block.

2. The method of claim 1, wherein introducing the gaseous bubble into the inlet port further comprises conveying the second liquid reagent to the inlet port to move the gaseous bubble into the inlet port in advance of the second liquid reagent.

3. The method of claim 1, wherein evaporating the portion of the second liquid reagent comprises heating the station block at a temperature of about 140° to about 150° degrees Fahrenheit for a period of about 7.5 to about 15 seconds.

4. The method of claim 1, wherein providing the gas space at the top of the inlet passage further comprises conveying pressurized gas into the inlet passage prior to mounting the flow cell on the station block.

5. The method of claim 1, wherein providing the gas space at the top of the inlet passage further comprises draining a portion of the second liquid reagent from the top of the inlet passage prior to mounting the flow cell on the station block.

6. The method of claim 1, wherein providing the gas space at the top of the inlet passage further comprises pumping a portion of the second liquid reagent from the top of the inlet passage prior to mounting the flow cell on the station block.

7. The method of claim 6, wherein pumping the portion of the second liquid reagent from the top of the inlet passage comprises removing the portion of the second liquid reagent with a variable-displacement chamber.

8. The method of claim 1, wherein conveying the second liquid reagent from the inlet passage into the inlet port to move the gaseous bubble through the flow path and into the outlet passage and fill the flow passage with the second liquid reagent comprises operating a suction pump located downstream of the outlet passage.

9. A method for operating a nucleic acid sequencing instrument having one or more movable flow cells, the method comprising:
   providing a flow cell comprising a flow path having an inlet port and an outlet port;
   providing a first station block having a first inlet passage and a first outlet passage;
   mounting the flow cell on the first station block to place the inlet port in fluid communication with the first inlet passage and the outlet port in fluid communication with the first outlet passage;
   pumping a first liquid reagent from the first inlet passage into the inlet port to fill the flow path with the first liquid reagent;
   removing the flow cell from the first station block;
   providing a second station block having a second inlet passage and a second outlet passage;
   mounting the flow cell on the second station block to place the inlet port in fluid communication with the second inlet passage and the outlet port in fluid communication with the second outlet passage;
   introducing a gaseous bubble into the inlet port by:
      evaporating a portion of a second liquid reagent located in the second inlet passage to create a gas space at a top end of the second inlet passage prior to mounting the flow cell on the second station block, and
      capturing gas in the gas space upon mounting the flow cell to the second station block to thereby form the gaseous bubble;
   pumping a second liquid reagent from the second inlet passage into the inlet port to move the gaseous bubble from the inlet port to the second outlet passage and to fill the flow path with the second liquid reagent; and
   removing the flow cell from the first station block.

10. The method of claim 9, wherein introducing the gaseous bubble into the inlet port further comprises pumping the second liquid reagent to the inlet port to move the gaseous bubble into the inlet port in advance of the second liquid reagent.

11. The method of claim 9, wherein evaporating the portion of the second liquid reagent comprises heating the second station block at a temperature of about 140° to about 150° degrees Fahrenheit for a period of about 7.5 to about 15 seconds.

12. The method of claim 9, wherein providing the gas space at the top of the second inlet passage further comprises conveying pressurized gas into the second inlet passage prior to mounting the flow cell on the second station block.

13. The method of claim 9, wherein providing the gas space at the top of the second inlet passage further comprises draining a portion of the second liquid reagent from the top of the second inlet passage prior to mounting the flow cell on the second station block.

14. The method of claim 9, wherein providing the gas space at the top of the second inlet passage further comprises pumping a portion of the second liquid reagent from the top of the second inlet passage prior to mounting the flow cell on the second station block.

15. The method of claim 14, wherein pumping the portion of the second liquid reagent from the top of the second inlet passage comprises removing the portion of the second liquid reagent with a variable-displacement chamber.

16. The method of claim 9, wherein pumping the second liquid reagent from the second inlet passage into the inlet port to move the gaseous bubble through the flow path and into the outlet passage and fill the flow passage with the second liquid reagent comprises operating a suction pump located downstream of the outlet passage.

17. The method of claim 9, wherein the steps of pumping the first liquid reagent and pumping the second liquid reagent comprise operating a single suction pump that is fluidly connected to the first outlet passage and the second outlet passage.

* * * * *